United States Patent [19]

D'Amelio et al.

[11] Patent Number: 4,823,791
[45] Date of Patent: Apr. 25, 1989

[54] ELECTROSURGICAL PROBE APPARATUS

[75] Inventors: Frank D. D'Amelio, Naugatuck, Conn.; Dawn M. DeLemos, Cornwall; Dominick G. Esposito, Mamaroneck, both of N.Y.; Michelle D. Maxfield, Norwalk, Conn.; Claude E. Petruzzi, Bronxville; Robert H. Quint, Jamaica, both of N.Y.

[73] Assignee: Circon ACMI Division of Circon Corporation, Stamford, Conn.

[21] Appl. No.: 47,666

[22] Filed: May 8, 1987

[51] Int. Cl.$^4$ .............................................. A61B 17/39
[52] U.S. Cl. .......................... 123/303.14; 128/303.17; 219/234
[58] Field of Search ...................... 128/303.13, 303.14, 128/303.15, 303.17, 800, 801; 219/234

[56] References Cited

U.S. PATENT DOCUMENTS

| | | | |
|---|---|---|---|
| 1,814,791 | 7/1931 | Ende | 128/303.17 |
| 3,746,814 | 7/1973 | Lackey | 128/303.14 |
| 4,033,351 | 7/1977 | Hetzel | 128/303.14 |
| 4,161,950 | 7/1979 | Doss et al. | 128/303.14 |
| 4,532,924 | 8/1985 | Auth et al. | 128/303.17 |
| 4,637,392 | 1/1987 | Sorochenko | 128/303.17 X |
| 4,765,331 | 8/1988 | Pettruzzi et al. | 128/303.14 |

FOREIGN PATENT DOCUMENTS

| | | |
|---|---|---|
| 2037167 | 7/1980 | United Kingdom . |
| 85/00280 | 1/1985 | World Int. Prop. O. ...... 128/303.14 |
| 85/03859 | 9/1985 | World Int. Prop. O. ...... 128/303.17 |

OTHER PUBLICATIONS

"The Heater Probe: A New Endoscopic Method for Stopping Massive Gastrointestinal Bleeding", pp. 257-262 of Gastroentology.
"Endoscope Thermal Treatment of Upper G.I. Bleeding", pp. 12-26.

Primary Examiner—Lee S. Cohen
Attorney, Agent, or Firm—Perman & Green

[57] ABSTRACT

A disposable bipolar electrosurgical probe which can be readily applied to the tissue to be treated, then discarded. The probe comprises an elongated substrate member having a peripheral surface of dielectric material and a longitudinal axis extending between a working end and an attachment end. At least a pair of electrically isolated electrodes extend continuously on the peripheral surface of the substrate member between an active region at the working end and an electrical terminal region at the attachment end for quick connection and/or disconnection, respectively, to opposite poles of an RF generator. A handle with a quick disconnect mechanism is provided to physically support the probe and enable it to be selectively energized. The probes can be of a fail safe construction so as to assure that only a proper probe can be used for a desired treatment.

44 Claims, 10 Drawing Sheets

FIG. 10A   FIG. 10B   FIG. 10BB   FIG. 10C
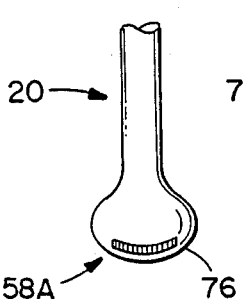
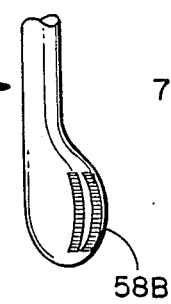
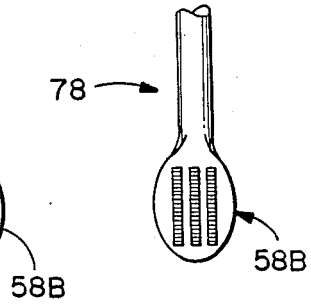
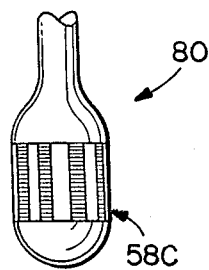
FIG. 10AA   FIG. 10BBB   FIG. 10D
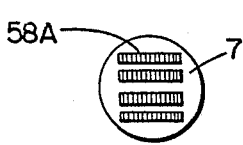
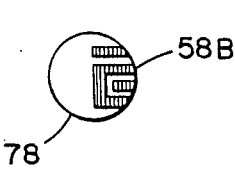
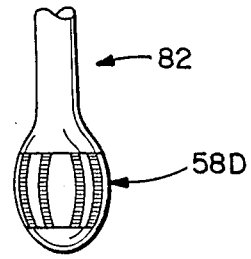
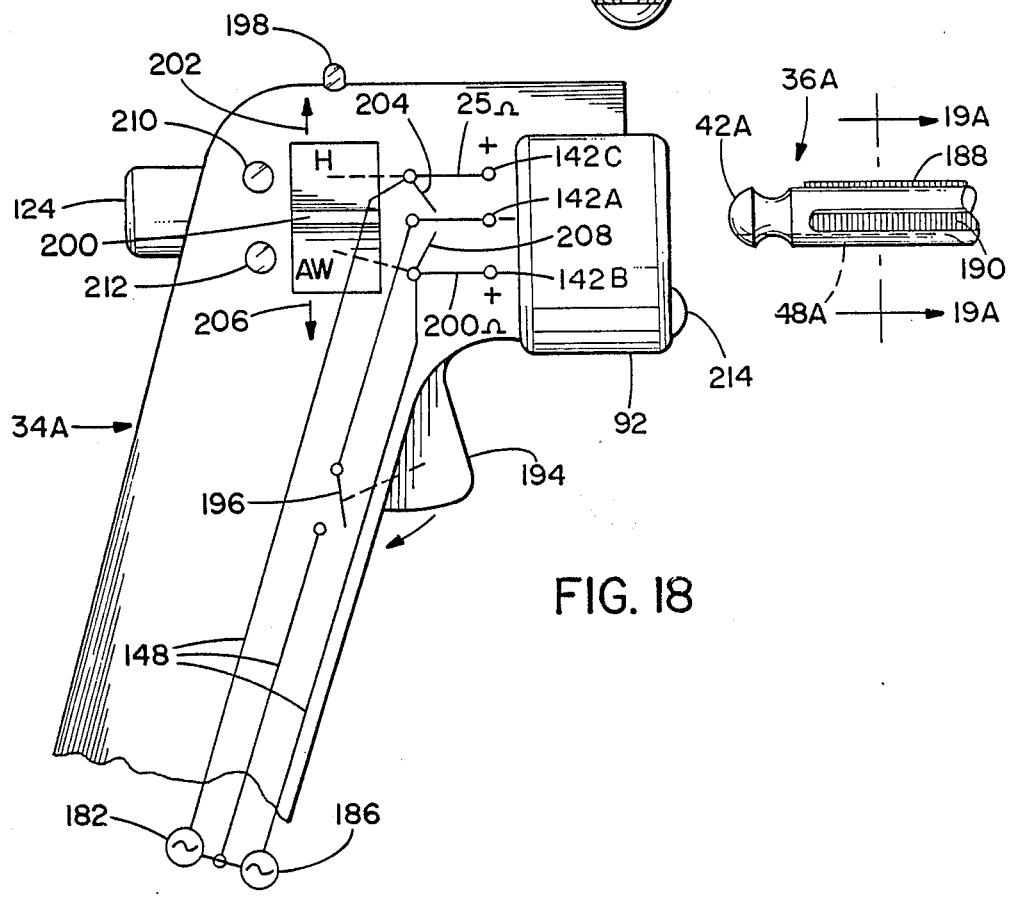
FIG. 18

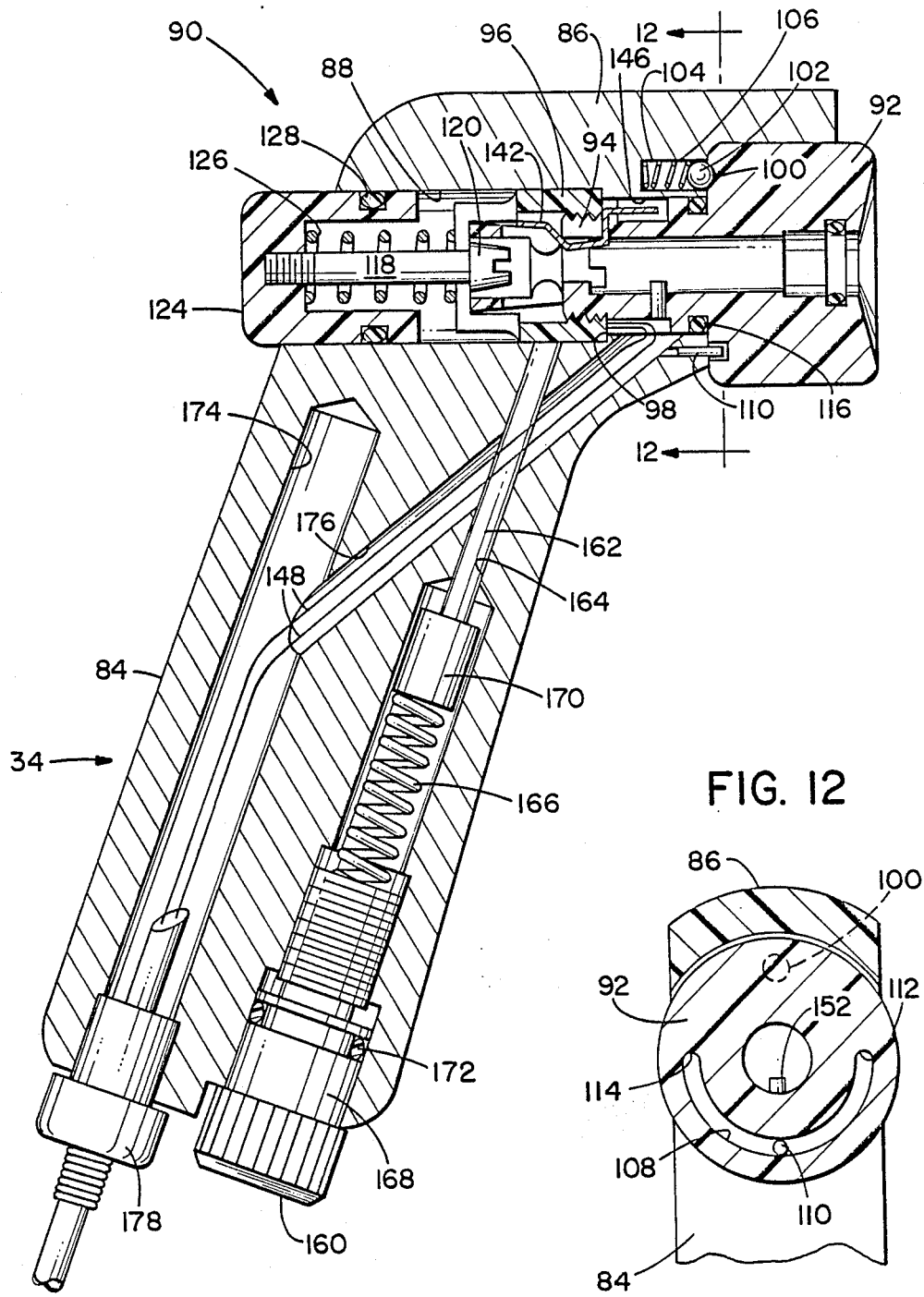

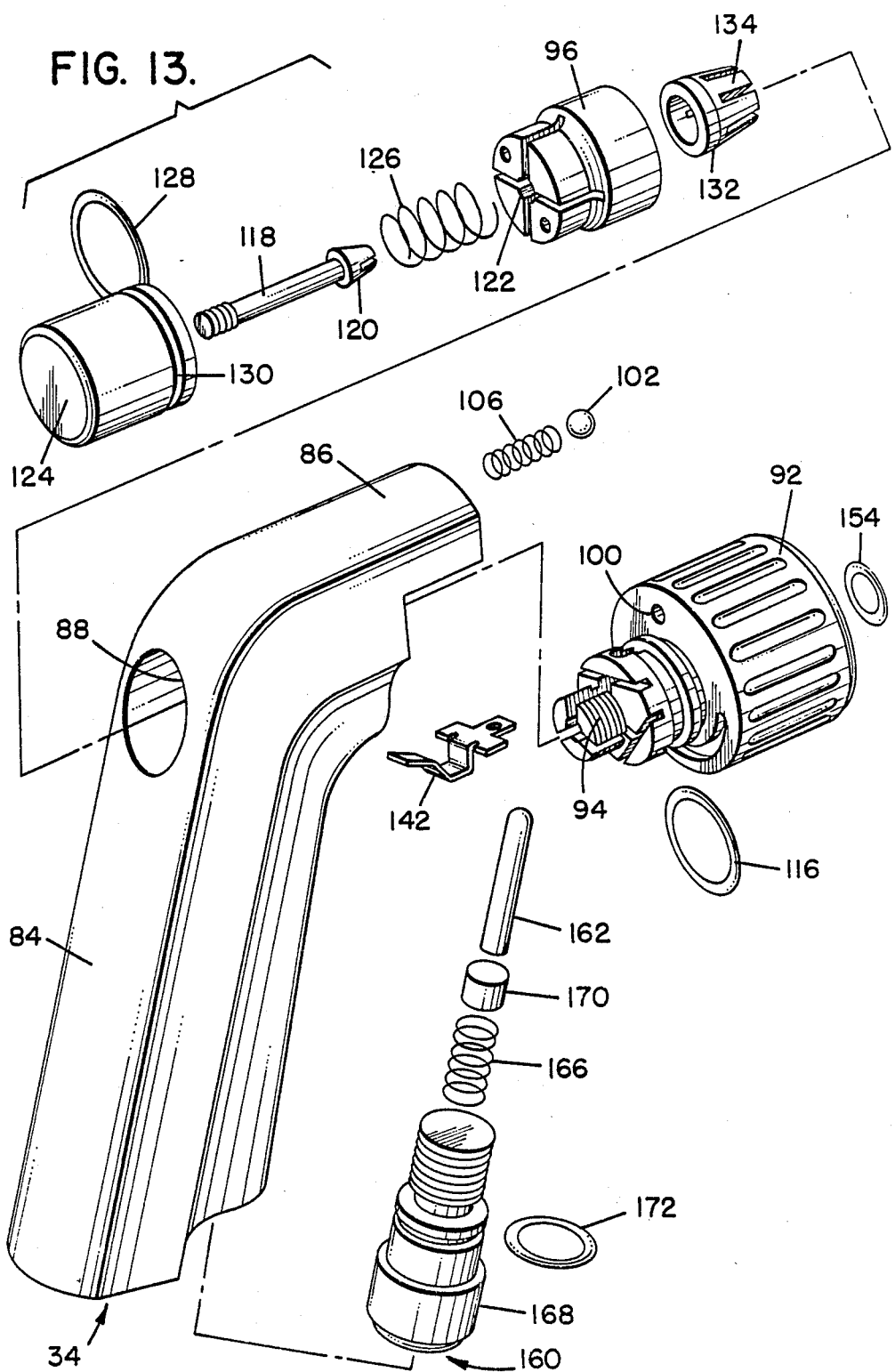

FIG. 14.
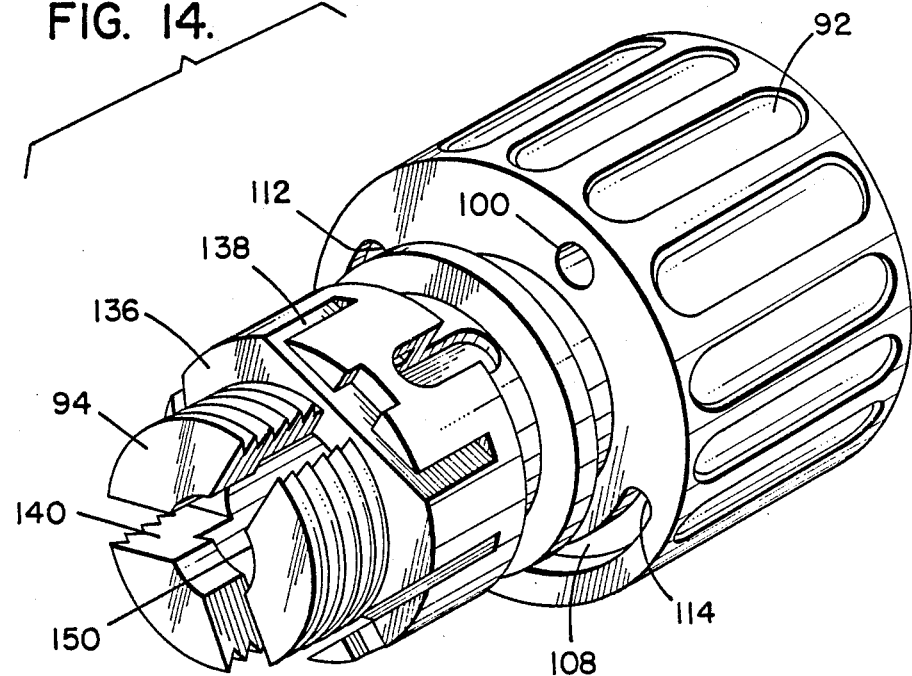
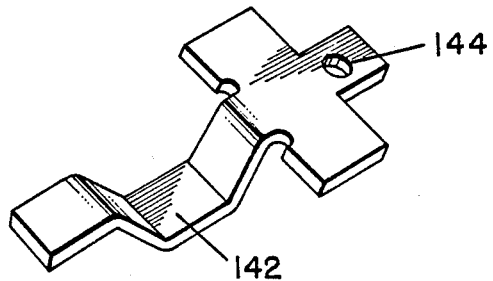

| PROBE | SWITCH | GENERATOR |
|---|---|---|
| 0 = CONTACT FOR HEMORRHOID TREATMENT<br>1 = CONTACT FOR ANAL WART TREATMENT | 0 = POWER TO CONTACT FOR HEMORRHOID<br>1 = POWER TO CONTACT FOR ANAL WART TREATMENT | 0 = NO POWER<br>1 = POWER |
| 0 | 0 | 1 |
| 0 | 1 | 0 |
| 1 | 0 | 0 |
| 1 | 1 | 1 |

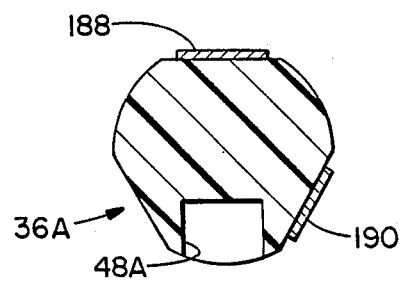
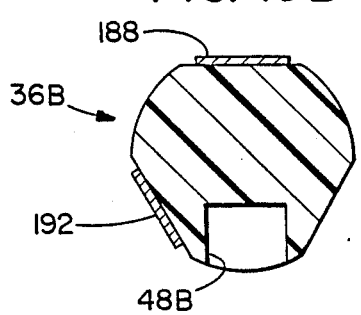
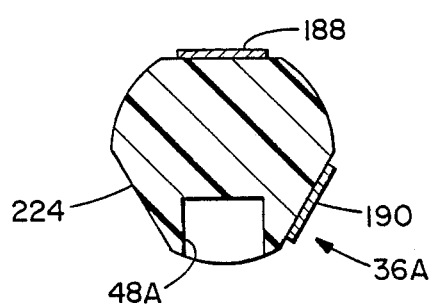
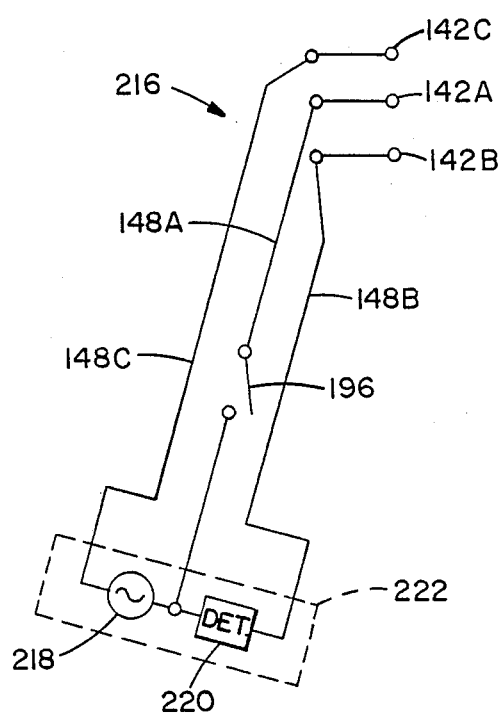
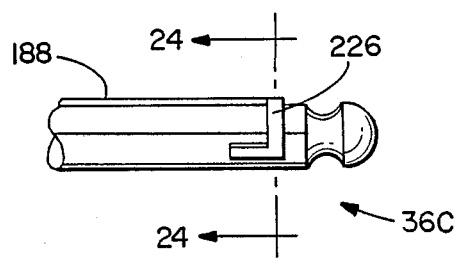
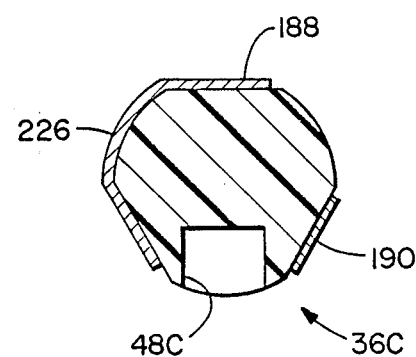

ELECTROSURGICAL PROBE APPARATUS

BACKGROUND OF THE INVENTION

1. Field of the Invention

This invention relates generally to electrosurgery and, more specifically, to a bipolar electrosurgical device for use in precision surgery. The device is an inexpensive, disposable, yet fully effective, probe body capable of performing focused treatment of the target tissue.

2. Description of the Prior Art

The use of heat for the cauterization of bleeding wounds dates to ancient times. In the present century, the use of radio frequency (RF) electrical current traveling through a portion of the body has been widely used to stop bleeding. Cauterization of tissue arises by virtue of its resistivity to RF energy. In the cauterization of blood, the proteins in it are heated to a temperature at which the proteins congeal in a manner similar to the process involved in the cooking of egg white. RF energy is preferred because its frequency is above that which could otherwise cause neuro-muscular stimulation Several modes of RF cauterization of tissue are employed, such as monopolar or bipolar coagulation In monopolar coagulation, an active electrode of small dimensions such as of the order of one to two millimeters is applied to the bleeding site and the current path is completed through the body to a distanced electrical return plate in contact with a large surface area of the body such as the buttocks. One technique in which the monopolar mode may be employed involves fulguration which is the use of a spark or arc from the active electrode to the tissue. In bipolar coagulation, the two active electrodes are closely spaced and are of the order of fractions of millimeters or larger so that the current path is confined to a local region of the tissue.

Another technique for stopping bleeding involves the delivery of thermal energy, such as from a resistively heated probe as described in an article entitled "The Heater Probe: A New Endoscopic Method For Stopping Massive Gastrointestinal Bleeding" by R. L. Protell appearing in Vol. 74, No. 2, Part 1, pages 257-262 of *Gastroentrology*, 1978.

A comparison of various coagulating techniques appears at pages 362-366 of an article entitled "Endoscope Thermal Treatment of Upper G.I. Bleeding", by J. H. Johnson, *Endoscopy Review*, July, 1986, pp. 12-26. Thus, it is well known that tissue proteins coagulate at temperatures of 50°-100° C.

The coagulation of bleeding vessels such as in the case of bleeding ulcers in gastrointestinal parts of the body generally requires use of a long endoscope from the distal end of which the bleeding area first must be identified and subsequently treated with an instrument passed through a channel provided in the endoscope. Locating the bleeding site is not easy since often the tissue wall being investigated may be moving, debris in the form of particles is likely to be present and interfere with vision and the blood flow itself tends to obscure the bleeding sources. These sources can be very small, of the order of less than a millimeter across, with many present in a particular area and each to be coagulated.

The endoscope, or the device inserted through it, therefore, is also provided with a wash channel through which a fluid such as a liquid or gas can be supplied to flush away the debris and permit visual scrutiny of the tissue area to be treated. In the above identified Endoscope Laser Treatment article, a flow of gas which is coaxial with the laser fiber is used to clear tissue. In a known electrosurgical device of the bipolar type, a pair of conductors are embedded in the wall of a catheter whose central bore is used to supply gas or liquid to the tissue area to be treated. The conductors project in the form of spaced-apart loops from a distal end of the catheter.

When a tissue area is to be treated, each tiny source of blood is subjected to heat treatment. This means the clearing of tissue with a wash of fluid, followed by the application of heat, again clearing the area and applying heat and so on until all of the bleeding areas have been coagulated. In such treatment, the repeated applications should be made with facility in an accurate manner with a minimum of undesirable side effects such as the sticking of the coagulating device to tissue areas.

The laser technique has the advantage of not requiring physical contact, and thus avoiding such sticking problems, but because of the variable way in which different tissue conditions permit absorption of the laser energy, precise control during tissue treatment is difficult. The monopolar electrosurgical device tends to injure tissue not intended to be treated and even cause damage in the target area itself such as by excessively deep effects in the target area. Hence, bipolar electrosurgical treatment of tissue has been proposed and used to improve safety inasmuch as the electric current is confined to the small area between electrodes. Over the years, numerous bipolar devices have been devised.

For example, starting with an early 1875 U.S. Pat. No. 164,184 to Kidder, a bipolar electrosurgical device is proposed wherein a pair of conductors are spirally wound onto a rubber probe body in which the conductors are embedded. The conductors are shown terminated at a distal hemispherically shaped end of the probe body. A thermally heated knife is described and shown in the U.S. Pat. No. 1,366,756 to R. H. Wappler who employed a pair of half-round cross-sectionally shaped conductor rods twisted about an insulator to connect to a heater-knife. In 1934, Kimble proposed a bipolar electrosurgical device in U.S. Pat. No. 1,983,669 wherein a pair of conductors are shown twisted around a common insulator and project from a retainer body in a manner useful for side-wise or head-on application to a tissue area.

The U.S. Pat. No. 4,011,872 to Komiya proposes an electrosurgical device wherein, for example, as shown in FIGS. 5, 9 and 11, one conductor is connected to a high frequency energy source and is formed of three or four electrodes. The electrodes individually extend from a distal end with spacings between electrodes being variable to accommodate or grasp differently sized tissue areas. In the U.S. Pat. No. 3,987,795 to Morrison, an electrosurgical device is described to operate in a mode which is intermediate the mono and bipolar modes of electrosurgery. This is achieved by mounting on one body, made of ceramic or glass, an active electrode and a return electrode whose surface area is made significantly larger than that of the active electrode. Various probe configurations are illustrated in the drawings.

Although these prior art electrosurgical devices are useful, they often do not provide satisfactory operation for a number of reasons. For instance, as previously noted, it is important that the probe body with which a cauterizing high frequency current is supplied can be repeatedly and precisely made to impinge upon the tiny blood vessel openings in the tissue area being treated independent of the orientation of the probe. This requires that as the probe is manually controlled at the proximal end of an endoscope, proper electrical contact is achieved to coagulate a blood vessel or other tissue target area whether the probe body is applied head-on, obliquely or side-wise to the tissue area.

Use of electrode configurations, as shown or described in the above prior art, thus frequently is unsatisfactory because of the larger number of probe applications needed to treat a tissue target or achieve coagulation of a bleeding tissue area.

The commonly assigned U.S. Pat. No. 4,532,924 to Auth et al discloses an improved electrosurgical device according to which a more consistent and accurate tissue treatment is obtained with a multiple bipolar probe body on which at least one pair of conductors is distributed in a predetermined manner. As described with respect to one embodiment, the probe body is sized so that it can be passed through a channel of an endoscope from its proximal end. The probe body is provided with electrodes which are branched to form a plurality of electrode strips. The electrodes of different conductors are selectively sized and generally uniformly distributed in spaced apart pairs, over the distal end and side of the peripheral surface of the probe body. The ratio of the width of the electrodes to the spacing between them is so selected as to provide, with a predetermined minimum number of spaced apart pairs of electrodes, omnidirectional multiple bipolar treatment of tissue when the probe body is operatively projected from the distal end of the endoscope.

The use of one or more pairs of electrodes of which may be branched to form a plurality of electrode strips assures at least bipolar or multiple bipolar tissue contact when the probe body is applied while the probe body is small enough to electrically coagulate the individual blood vessels from the distal end of an endoscope. A particularly effective probe body in accordance with the invention disclosed in commonly assigned U.S. Pat. No. 4,765,331 issued Aug. 23, 1988 entitled "Focused Treatment Probe" employs at least six electrode strips from one or more pairs of electrodes, constituting the equivalent of six bipolar coagulating devices, around the peripheral surface of the endoscopically passable probe body. With such an electrosurgical device, two or more of the electrode strips make tissue contact independent of the orientation of the probe body for effective treatment of tissue. That invention is particularly applicable to the treatment of cancerous tumors such as in the esophageal, rectal or anal areas, and may also be used for the treatment of hemorrhoids, although it is applicable to treat tissue in a wide range of other body locations as well, both internal and external. In all of these applications the area to be treated is usually only a portion of the wall of the duct and thus the instrument minimizes harm to healthy tissue adjacent to the cancerous area by appropriately locating the electrodes on the probe body.

SUMMARY OF THE INVENTION

The present invention represents yet a further improvement over such known bipolar electrosurgical devices. It has become increasingly desirable to be able to insert a probe body into the cavity or duct of the human body with minimal trauma and resulting pain to the patient being subjected to the treatment. At the same time, less expensive constructions of treatment devices are constantly being sought as well as constructions which are disposable to thereby avoid contamination and the high cost of sterilization. In each instance, as well, it is necessary to properly focus the electrical energy so as not to injure tissue not intended for treatment. The present invention achieves all of these goals, and is especially concerned with the treatment of tissue generally in the anal region. Thus, the present invention may be used for treatment of rectal tumors which are typically located a substantial distance upstream of the anal opening, hemorrhoids which are typically located just inside the anal opening, and condolomata, also known as anal warts, which are typically located externally of the anal canal and in the annular region surrounding the anal orifice.

The concern for treatment of hemorrhoids is particularly acute since it is estimated that one out of every two Americans over the age of forty suffers from hemorrhoids and, dependent on the degree of severity, many of these seek medical attention. Methodologies of treatment currently range from surgery to the application of topical ointments.

Anatomically, hemorrhoids are basically outpocketed varicose veins. More specifically, they are a node of nested, feeding arteries and interlaced veins that, due to a multitude of mechanisms, both known and unknown, including strain and abrasion, have outpocketed into the bowel duct. This outpocketing has a deleterious, avalanching effect, that is, the outpocketed area has increased its exposure to the point that extreme swelling, bleeding or even prolapsing can occur. The medical challenge presented is to stop the blood flow into these outpocketed packets. This can be accomplished in any one of three ways: (a) surgically remove the area, (b) stricture the area (that is, significantly reduce its blood flow) and (c) either chemically or thermally sclerose the area.

Surgical intervention is considered the least favorable option, as it requires long hospital stays, along with the inherent risk of surgery. Stricturing the area is typically accomplished with bands in the nature of O-rings involving pain upon application and the requirement that the bands remain in place for two to three days until the area dries up and "sluffs off" due to lack of blood flow. Chemically sclerosing the area, typically with the injection of alcohols, has proven to be painful. Thermally sclerosing the area includes freezing with liquid nitrogen which causes painful swelling, or elevating the temperature via the use of infra red (IR) energy. While IR coagulation is effective, its application en face and the energy thus applied is poorly distributed over the area being treated. Another option is bipolar technology which has proven to be a particularly effective tool in the treatment of hemorrhoids without the limitations and complications inherent in the above mentioned forms of treatment.

Another item of substantial concern with respect to treatments in fluid issuing regions of the body and, notably, the anal region, is the fear of cross-contamination of communicable diseases including, but not limited to, hepatitis and AIDS. Although the fear of cross-contamination of the deadly AIDS virus has been known and scantily stated in medical periodicals, no effective barrier-like method has been developed for the medical products used in this area. Thus, only a disposable product truly alleviates the fear of cross-contamination.

The invention, therefore, is directed toward a unique, disposable bipolar electrosurgical probe which can be readily directed at the tissue to be treated, then discarded when the treatment has been completed. A part of the invention also resides in the provision of a handle in the form of a pistol grip which permits ready connection of the probe with a conventional electrical generator. It is anticipated that the handle be a permanent, non disposable item having a construction enabling a probe to be rapidly attached to and rapidly detached from the handle. Also, a switch may be incorporated into the handle to assure a rapid connection to and disconnection from the output of an electrical generator, together with an appropriate indicator to inform the user whether the probe is energized or not. The invention also makes provision for the use of different probe designs for different types of abnormalities, both internally and externally of the body. Such different treatments may require different parameters for the electrical energy being applied to the tissue to be treated and the system accommodates such a requirement in an effective and fail-safe manner.

Thus, the device comprises a bipolar probe body which may be utilized for the treatment of either external or internal body tissue. In the event the tissue to be treated is located internally, the device is sized for passage into and within a body cavity with or without the aid of an endoscope, anoscope, or the like. The probe body includes an elongated dielectric substrate with an active member at one end for providing focused treatment of tissue and an attachment end opposite the active member for connection with a source of electrical energy. The active member may be generally cylindrical shaped, barrel shaped, arcuate shaped or any other functional shape, and may have a peripheral surface on which are mounted a plurality of electrodes, those of one polarity being interposed with those of the opposite polarity. The length of the electrodes can be chosen to obtain desired longitudinal focusing, and the electrodes can also be branched into several electrode strips and positioned within a restricted arc to obtain desired peripheral focusing. Additionally, an electrically insulative covering covers the mid regions of the probe to permit handling of the probe body without obstructing the attachment end and the working end. The covering also serves to mark at least one of the boundaries of the active region made up of a plurality of electrodes.

The invention has numerous features and benefits. These include an electrosurgical probe which is of unitary construction employing no moving parts and therefore requiring no physical assembly. As a result, it provides much improved reliability over prior constructions, assures the fabrication of a more consistent end product which, in turn, provides more consistent results than its predecessors, is less labor intensive in its construction and utilizes cost effective materials. Additionally, the probe is lighter in weight than its predecessors and, indeed, can be so readily and inexpensively manufactured as to be disposable. As a result of all the aforesaid features and benefits, individual probes can be provided for specific types of treatment at a price which will enable a physician or other user to employ a particular probe intended for a specific treatment. Previously, because of the relatively high cost of probes, a physician or other user often times used a probe which was optimized for one type of treatment for another type of treatment for which it was not optimized. While, in most instances, this was a medically permissible procedure, the most desirable results were not always achieved.

Other and further features, objects, advantages, and benefits of the invention will become apparent from the following description taken in conjunction with the following drawings. It is to be understood that both the foregoing general description and the following detailed description are exemplary and explanatory but not restrictive of the invention. The accompanying drawings which are incorporated in, and constitute a part of the invention, illustrate different embodiments of the invention and, together with the description, serve to explain the principles of the invention in general terms. Like numerals refer to like parts throughout.

DETAILED DESCRIPTION OF THE DRAWINGS

FIGS. 1A, 1B, and 1C are detail views illustrating different procedures which can be performed by the invention;

Figure 9:
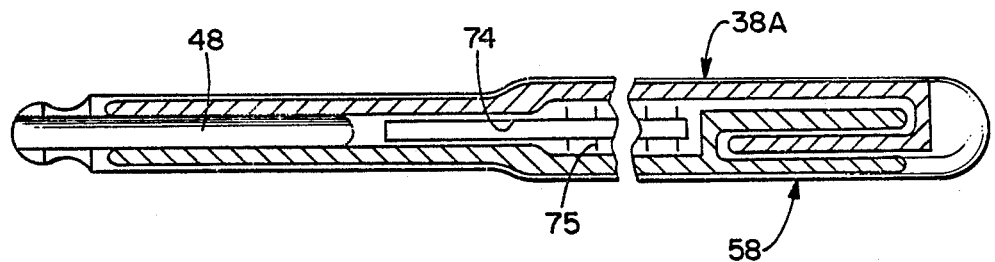
Figure 5:
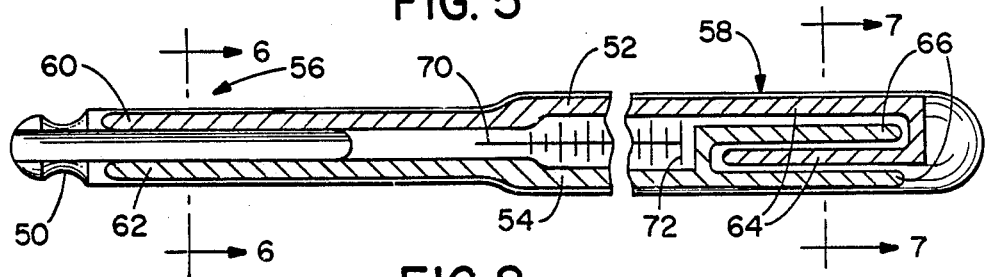
FIG. 5 is a top plan view of a probe substrate with metallization thereon in accordance with the invention.
Figure 8:
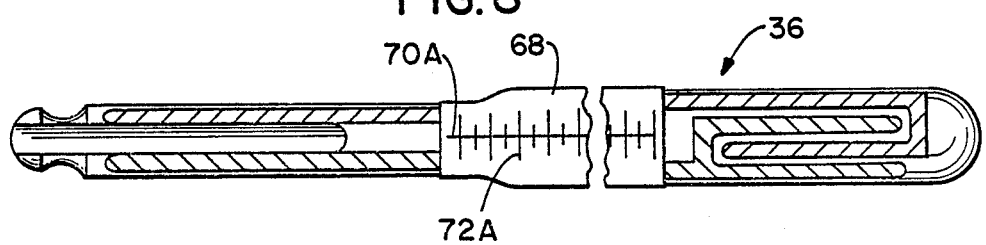
Figure 6:
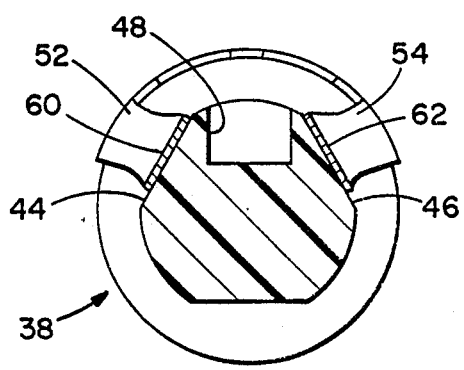
Figure 7:
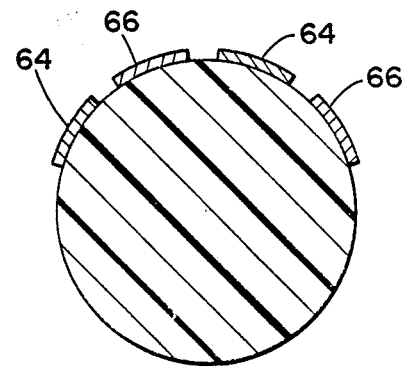
Figure 15:
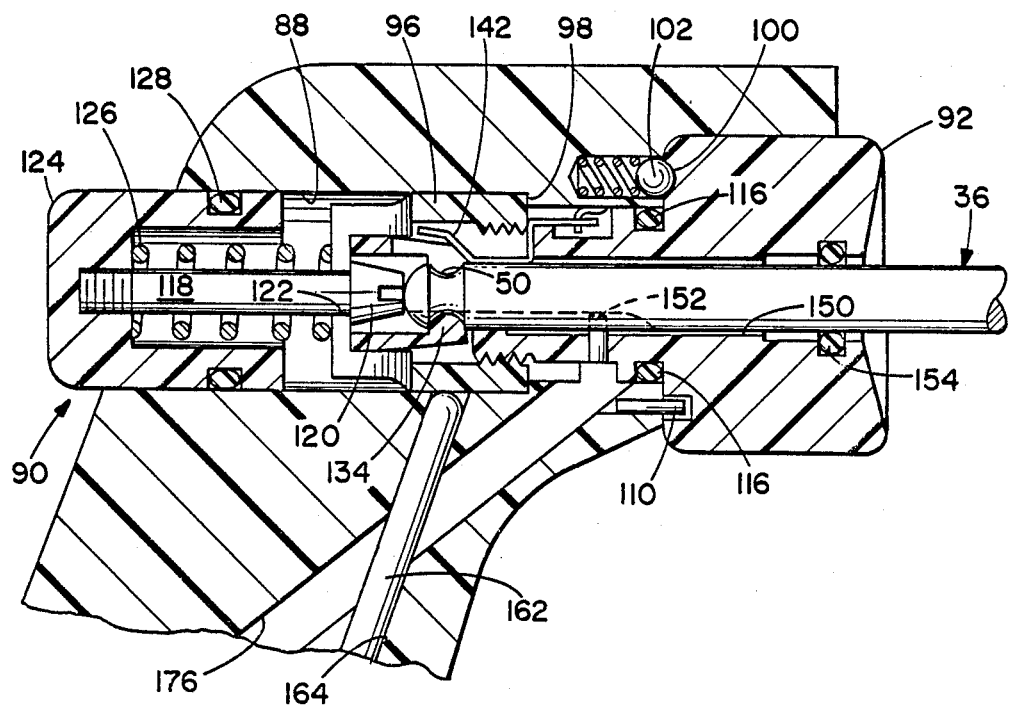
Figure 16:
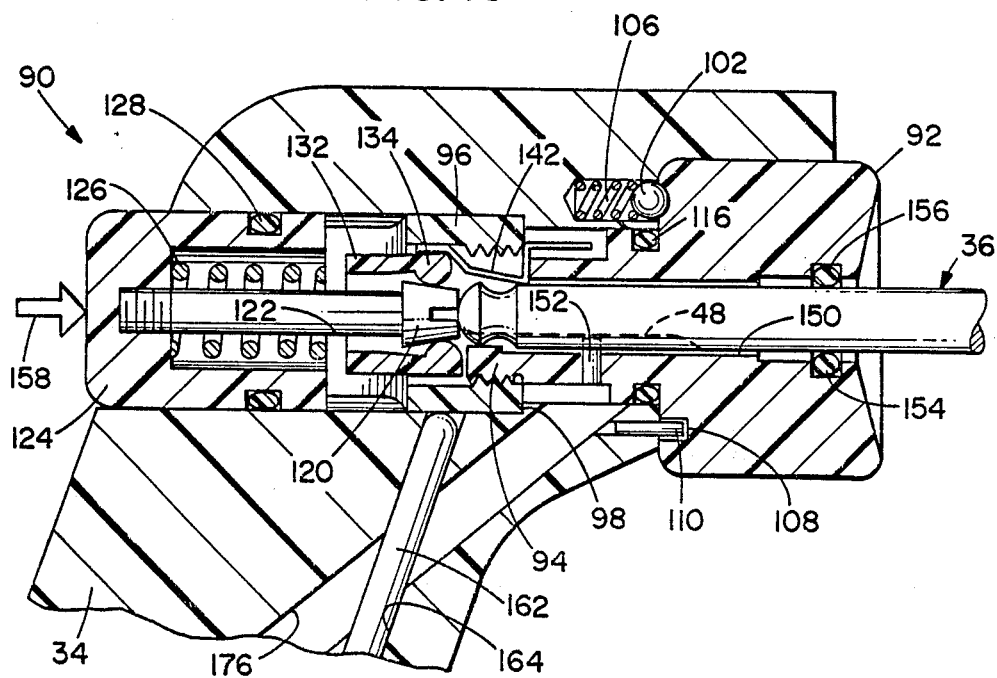
Figures 17, 20:
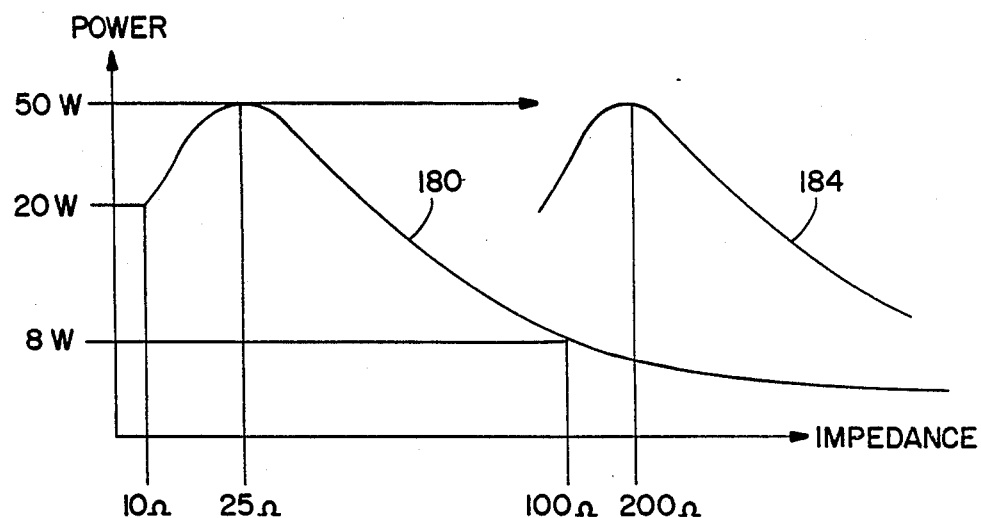

FIGS. 6 and 7 are cross section views taken, respectively, along lines 6—6 and 7—7 in FIG. 5;

FIG. 8 is a top plan view, similar to FIG. 5 but illustrating an outer dielectric covering thereon;

FIG. 9 is a top pl an view, similar to FIG. 5 illustrating another embodiment of an electrosurgical probe according to the invention;

FIGS. 10A and 10AA are detail plan and elevation views, respectively, of the working end of an electrosurgical probe according to the invention;

FIGS. 10B, 10BB, and 10BBB are detail side elevation, plan, and end elevation views, respectively, of the working end of another electrosurgical probe according to the invention;

FIGS. 10C and 10D are detail plan views of various working ends of still other electrosurgical probes according to the invention;

FIG. 11 is a side elevation view, in cross section, of a handle member for the electrosurgical treatment system according to the invention;

FIG. 12 is a detail cross section view taken along line 12—12 in FIG. 11;

FIG. 13 is an exploded perspective view of the handle member illustrated in FIG. 11;

FIG. 14 is an enlarged perspective view of components illustrated in FIG. 13;

FIGS. 15 and 16 are detail cross section views illustrating a portion of the handle member illustrated in FIG. 11, and further illustrating different positions thereof;

FIG. 17 is a graph illustrating the operational characteristics of electrical generating devices required for purposes of the invention;

FIG. 18 is a diagrammatic view illustrating another embodiment of the invention;

FIG. 19A is a cross section view taken generally along line 19A—19A in FIG. 18;

FIG. 19B is a cross section view, similar to FIG. 19A, illustrating a probe suitable for a different condition than the probe of FIG. 19A;

FIG. 20 is a truth table for explaining the operation of the embodiment illustrated in FIG. 18;

FIG. 21 is an electrical schematic diagram illustrating another embodiment of the invention;

FIG. 22 is a cross section view substantially similar to FIG. 19A;

FIG. 23 is a detail side elevation view of a modified probe; and

FIG. 24 is a cross section view taken generally along line 24—24 in FIG. 23.

DETAILED DESCRIPTION OF THE PREFERRED EMBODIMENTS

Figure 1A:
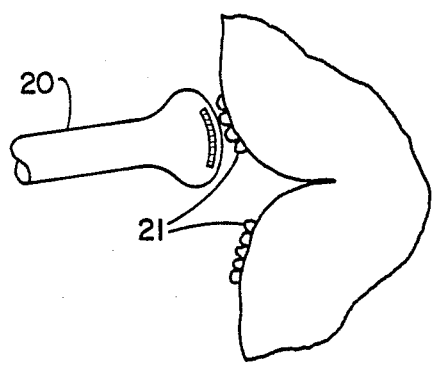
FIG. 1D is a detail view illustrating a different mode of performing the procedure illustrated in FIG. 1C.
Figure 1B:
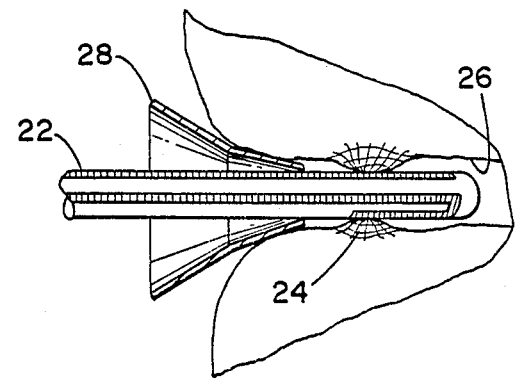
Figure 1C:
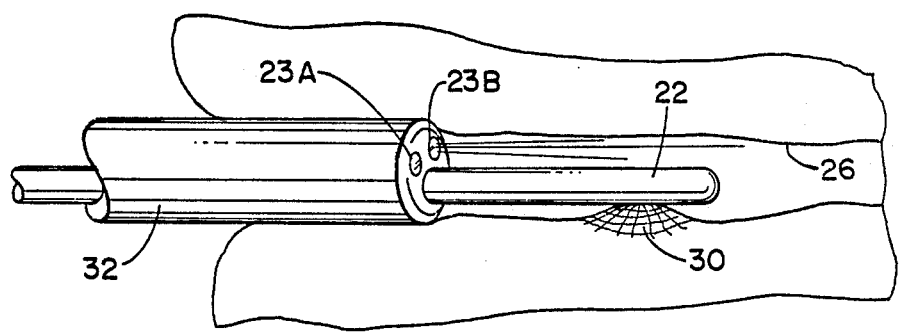
Figure 1D:
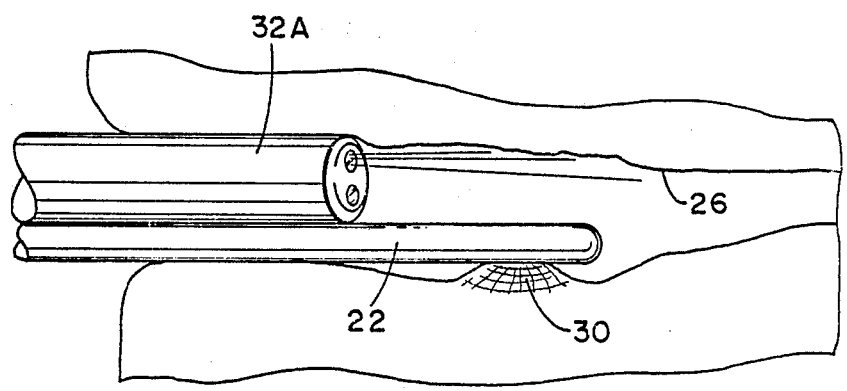

Turn now to the drawings and, initially, to FIGS. 1A, 1B, and 1C which are generally illustrative of electrosurgical probe apparatus which embodies the invention. While the invention is disclosed as being primarily applicable to the treatment of tissue in the anal regions of the body, it is not intended that the invention be so limited in its scope but may be used to treat both internal tissue and external tissue in many other regions of the body as well.

In one typical application, an electrosurgical probe 20 is utilized for treating condolomata, or anal warts 21, which sometimes develop on the external skin in the region of the anal opening. In FIG. 1B, another form of the probe, referred to herein by reference numeral 22, is employed for the treatment of hemorrhoids 24 which are normally located just inside the rectum 26. In this instance, an anoscope 28 is used to help guide the probe 22 and to open the rectum 26 sufficiently to provide the necessary visibility for treatment of the hemorrhoids.

In the instance depicted in FIG. 1C, the probe 22 is shown being used to treat a rectal tumor 30 which is typically located in the rectum 26 a substantial distance upstream of the anal opening. Because of the longer distance involved from the anal opening in the FIG. 1C situation, it may be desirable to use an endoscope 32. The endoscope may serve to guide the probe 22 in a known manner and to provide the illumination necessary, via a suitable light source 23A, and the visibility necessary, via a suitable visual port 23B, for the physician or other operator of the probe apparatus. FIG, 1D is illustrative of the use of an endoscope 32A similar to the endoscope 32, but without a lumen for receiving the probe 22. Instead, the probe is inserted into the rectum side by side with the endoscope 32A for treating the tumor 30 in the same manner as in the FIG. 1C situation.

For any or all of the procedures just described, it may be desirable to use a handle member 34 for releasably supporting the probe 22, or other suitable probe, during the treatment procedure. The handle member 34 will be described in greater detail subsequently.

Figure 3:
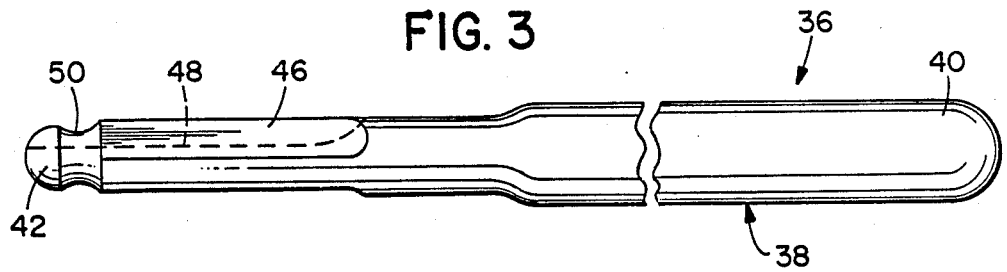
FIGS. 3 and 4 are side elevation and to plan views, respectively, of a probe substrate embodying the invention.
Figure 4:
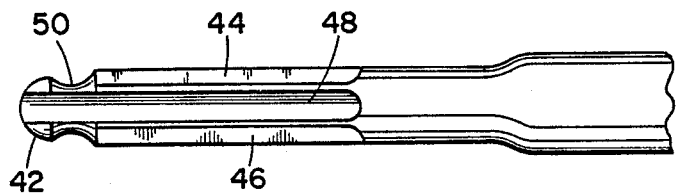

Turn now to FIGS. 3-9 which depict a primary component of the present invention, specifically, an electrosurgical probe 36. FIGS. 3 and 4 depict a unitary elongated substrate member 38 having a peripheral surface of plastic dielectric material although various other compositions such as ceramics, composites, or metals coated with a dielectric material would be suitable for the purposes of the invention. The probe 36 may be of a variety of shapes and cross sections although in the drawings it is illustrated as having a rounded peripheral surface and a longitudinal axis which extends between a working end 40 and an attachment end 42. At 1 ea st a pair of circumferentially spaced, longitudinally extending, flattened surfaces 44, 46 are formed in the peripheral surface of the substrate member 38 adjacent the attachment end 42. Also formed adjacent the attachment end 42, for purposes which will be subsequently described, are a longitudinal groove 48 parallel to, and generally coextensive with, the flattened surfaces 44 and 46, as well as an annular groove 50.

Figure 2:
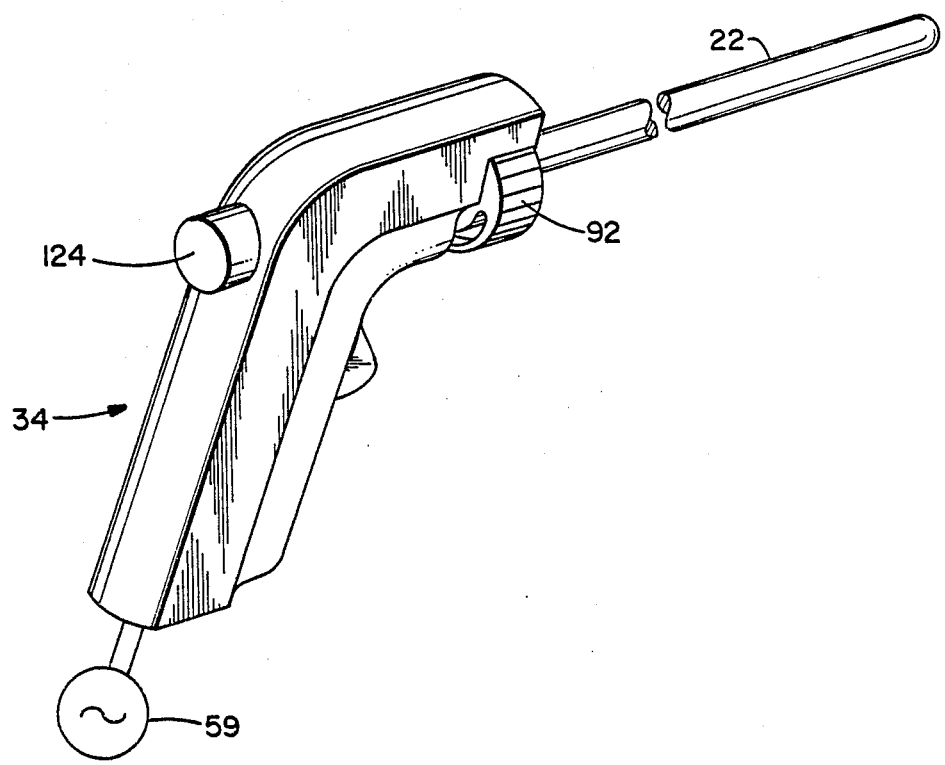
FIG. 2 is a perspective view of an electrosurgical treatment system according to the invention.

As seen particularly well in FIG. 5, at least a pair of continuous electrically isolated electrodes 52 and 54 are formed on the peripheral surface of the substrate member 38. For purposes of the invention, the term "electrode" is broadly intended to refer to an uninsulated conductor. The electrodes extend between an electrical terminal region generally at the attachment end 42 for connection, respectively, to opposite poles of a source 59 of electrical energy (FIG. 2) in a manner to be described and an active region at the working end 40 for providing focused treatment of the tissue. The source 59 is, specifically, an RF ("radio frequency") generator of known design. The locations at which the electrodes 52 and 54 extend onto the flattened surfaces 44 and 46, respectively, may be referred to as contact areas 60 and 62 for reasons which will become clear as the description of the invention proceeds. The electrodes 52 and 54 are composed of a conductive material such as copper, silver, or gold which is deposited on the peripheral surface of the substrate member 38 in any suitable manner. Techniques of thick and thin film circuitry utilized in printed circuit board manufacturing are suitable for the purposes of the present invention. However, various other processes for applying conductive material to three dimensional substrates would be acceptable for purposes of the invention.

As seen in FIGS. 5, 7, and 8 each of the electrodes 52 and 54 branches into a plurality of electrode fingers 64 and 66, respectively, at the active region 58. The electrode fingers 64 are interposed with the electrode fingers 66. All manner of relationships between the widths of each of the fingers 64 and 66 are possible as well as the spacing between adjacent electrode fingers. For example, the electrode fingers can be of fixed width while the spacing between them is variable; or they can be of variable width while the spacing between them is fixed or both width and spacing may be constant or may be variable. In any event, the ratio of the width of the electrode fingers to the spacing between adjacent electrode fingers is so selected as to enable effective bipolar treatment of tissue for a broad range of applications. For example, the relative number, width, length and spacing of the electrode fingers 64, 66 can be such as to precisely focus in on a limited tissue area or can be such as to provide substantially omnidirectional orientations of the active region 58 relative to the tissue to be treated.

It will be appreciated that the plastic substrate member 38 provides thermal isolation for the electrodes 52 and 54 as well as electrical isolation. At the same time, these benefits are achieved in a one piece member which does not require the use of wires and other separate components in its construction. Wires can easily be broken or misapplied and greater numbers of components add steps to the manufacturing process and a greater possibility of incorrect assembly. Thus, the invention results in lower assembly and piece part costs.

An outermost dielectric covering 68 (FIG. 8) may be provided over the substrate 38 and electrodes 52 and 54 thereon so as to extend between the working end 40 and the attachment end 42. One purpose for the dielectric covering is to permit handling of the substrate member 38 without obstructing the attachment end and the working end. Another purpose is to provide electrical and thermal insulation which permits safe handling of the probe. The covering 68 may be, for example, heat shrinkable polyurethane of sufficient thickness to protect the surface of the metallized substrate member 38 but without adversely increasing its diameter.

FIGS. 1B and 1C illustrate instances in which the electrosurgical probe of the invention is intended to be inserted into a body cavity. In order to perform the electrosurgical procedure, it is necessary for the physician or other operator of the apparatus to move the probe both along its longitudinal axis and rotationally about its longitudinal axis. It is therefore highly desirable for the probe to be provided with suitable markings both for indicating the depth of the probe within the body cavity and for indicating the position of the active region 58 within the body cavity. Accordingly, as seen in FIG. 5, a centrally disposed and longitudinally extending marking 70 may be provided as a base line for determining rotational movement of the probe. Also, a plurality of transverse markings 72 suitably provided on the peripheral surface of the substrate member 38 are helpful in determining the depth to which the probe has penetrated into the body cavity. The markings 70, 72 may be printed on or etched into the substrate member 38, or the substrate member may be molded with the markings already in place.

As seen in FIG. 8, such markings 70A and 72A may also be provided on the dielectric covering 68. It may be desirable for the markings to be painted on the substrate member 38 or on the dielectric covering 68 so as to be visible. For example, black markings on a white background or the use of other contrasting colors is beneficial. It might also be desirable to form topographical markings on the substrate member or dielectric covering. That is, the markings would either be formed so as to be raised above the surrounding surface or indented relative to the surrounding surface. Another expedient to provide sufficient visibility to properly orient the probe 36 inside a body cavity is to provide the substrate member 38 with a coloring which would contrast highly with the color of the electrode fingers 64 and 66 at the active region 58. For example, the colors of silver, gold, or copper which are typical electrode materials would contrast with a blue substrate member.

As seen in FIG. 9, it may even be desirable to form a modified substrate member 38A, as by a molding process, with a longitudinally extending end relatively deep groove 74 therein which would be indicative of a center line for the active region 58. In this instance, the groove 74 would replace the need for the longitudinal markings 70 or 70A. Also, suitable transverse markings 75 may be provided in combination with the groove 74.

Turn now to FIGS. 10A–10D which illustrate different shapes of probe bodies, and specifically of working ends therefor, which can be utilized with the invention. In FIGS. 10A and 10AA, the probe 20 which was previously illustrated in FIG. 1A, terminates at an enlarged working end having a blunt, but generally rounded, forward facing surface 76 containing an active region 58A lying in a plane generally transverse of the longitudinal axis of the probe (see FIG. 10AA). Such a probe is desirable for treating external tissue which is readily seen and accessible and the active region may be selectively sized according to the area of tissue to be treated.

In FIGS. 10B, 10BB, 10BBB, a probe 78 is illustrated which has a working end which is off set or eccentric relative to a longitudinal axis thereof. In this instance, an active region 58B is side looking and can be arcuate in either a longitudinal direction or circumferentially, or both. Such a design enables, in some instances, a deeper, better directed, and more uniform electrical flux penetration of the tissue being treated. Again, the active region 58B may be selectively sized according to the area of tissue to be treated.

FIG. 10C is illustrative of a more bulbous cylindrical design of working end than that provided by the probe 36 and with an active region 58C which possibly covers a greater circumferential arc than does the probe 36. FIG. 10D illustrates a probe 82 with a working end whose shape may be generally considered to be a combination of those of probes 78 and 80 in an effort to combine the benefits of each. These and other designs may be beneficially used with the apparatus of the invention and enable the invention to be applicable to treat a wide variety of tissue abnormalities. As with the preceding embodiments, the active region may be selectively sized according to the area of tissue to be treated.

Turn now to FIGS. 11–15 for a more detailed description of the handle member 34 which is used for supporting and energizing the electrosurgical probes of the invention. The handle member 34 may be of any suitable dielectric material for the purposes of the invention, plastic being such a material which can be relatively low in cost and relatively easy to fabricate. The handle includes a pistol grip portion 84 which is properly sized and shaped for the hand of the physician or other operator and a support portion 86 at the upper end of the pistol grip. A bore 88 extends through the support portion 86 and serves to receive and hold therein a lock-eject mechanism 90. The lock-eject mechanism 90, in turn, serves to receive, hold, then eject an electrosurgical probe 36, as desired.

To this end, a probe housing 92 is received at a forward end of the bore 88 and has a threaded stud 94 at its rearmost end. The stud 94 is threadedly engaged with a vise member 96 received in the bore 88 from its aft end. The vise member 96 bears against an annular shoulder 98 formed in the bore 88 thereby enabling the probe housing 92 to be held against longitudinal movement relative to the handle member 34. However, the probe housing 92 may be rotatable about its longitudinal axis and may turn the vise member 96 with it. A rear face of the probe housing 92 (FIG. 12) is formed with a detent 100 shaped and sized to receive a ball 102 received in a small bore 104 formed in the support portion 86 whose axis is generally parallel to that of the bore 88. A spring 106 biases the ball 102 in the direction of the probe housing 92. When the ball 102 is seated in the detent 100, a neutral position of the probe housing 92 is indicated. However, the probe housing can be rotated thereby forcing the ball 102 out of the detent 100 and compressing the spring 106 (see FIG. 13).

Also formed in the rear face of the probe housing 92 is an arcuate groove 108 which is generally concentric with the outer peripheral surface thereof (see FIG. 12). A generally longitudinally extending stop pin 110 is fixed to the support portion 86 and freely received in the arcuate groove 108. The groove 108 has opposite limits 112, 114, (FIG. 12) such that as the probe housing 92 is rotated out of its neutral position, the limits 112, 114 will strike the stop pin 110 and thereby define the extreme rotational positions of the probe housing relative to the reference position. Unlimited rotation of the housing 92 may also be achieved by omission of the limiting stop 110 and the replacement of the electrical wired connection by a slip rotary electrical contact system such as might be performed by a standard commutator. An O-ring seal 116 is suitably seated on the probe housing 92 and in engagement with the bore 88 to seal the interior of the lock-eject mechanism 90 against entry of dirt and moisture which would have a deleterious effect on its operation.

Refer now to FIG. 13. An eject pin 118 threaded at its aft end and having an enlarged conical head 120 at its opposite, forward end extends slidably through an aperture 122 formed at the aft end of the vise member 96. The aft end of the eject pin 118 is threadedly joined to a cup shaped eject button 124 which, in turn, is slidably received in the bore 88. A compression spring 126, generally coaxial with the eject pin 118, is interposed between the vise member 96 and the eject button 124 thereby biasing the button to an inactive, extreme leftward, position as depicted in FIG. 15. Similar to the probe housing 92, the eject button 124 is also provided with an O-ring seal 128 receivable in an annular groove 130 and interposed between the button 124 and the bore 88. The seal 128 serves a purpose similar to that of the seal 116.

Received within and generally concentric with the vise member 96 is a vise tube 132 provided with a plurality of integral forward extending fingers 134, each terminating at an enlarged gripping element.

The probe housing 92 includes a generally cylindrical contact seat member 136 (see especially FIG. 14) positioned adjacent the threaded stud 94. Three slots 138 are formed in the contact seat member 136 at equidistant circumferential locations about the contact seat member 136. The slots 138 lie in planes which, respectively, are parallel to the longitudinal axis of the probe housing 92 and include a chord of an exposed face of the contact seat member 136. Also, three radial slots 140 associated with each of the slots 138 are formed in the threaded stud 94. Each slot 140 lies in a plane perpendicular to its associated slot 138. A suitably shaped spring contact 142 is received through each pair of slots 138, 140 and has a connection tail 144 which extends into a suitable recess 146 whereat it can be connected as by solder to an associated wire lead 148 (see FIG. 11).

It should now be explained that the probe housing 92 has a centrally disposed longitudinally extending bore 150 which extends its entire length for loosely receiving therethrough an electrosurgical probe 36. A key pin 152 is fixed to the probe housing 92 and extends radially into the bore 150. It was previously explained that the substrate member 38 is formed with a longitudinal groove 48. Thus, as the probe 36 is inserted into the bore 150 it must be rotated about its longitudinal axis so as to align the groove 48 with the key pin 152. In this manner, the probe 36 is held rotationally fixed with respect to the probe housing 92. An O-ring seal 154 is seated in an annular recess 156 formed in the bore 150 and serves both to support the probe 36 and to prevent entry of dirt and moisture into the interior of the lock-eject mechanism 90.

When the probe 36 is fully inserted into the bore 150, that is, when it is in its operational position, the annular groove 50 lies in a plane of and is engaged by the enlarged gripping elements of the fingers 134 of the vise tube 132. In this position, the probe is firmly held against inadvertent removal from the handle member 34. It is supported at two spaced locations, that is, at the groove 50 and downstream therefrom by means of the O-ring seal 154. Furthermore, the probe 36 is so positioned by reason of the interrelationship between the groove 48 and the key pin 152 that the contact areas 60 and 62 are each mechanically and electrically engaged with an associated contact 142. It will be understood that while three pairs of slots 138, 140 have been described as being received by the contact seat member 136, in actual fact for purposes of the present embodiment, only two spring contacts 142 are actually operational. Another embodiment, to be described, will explain a purpose for the third contact.

At such time that it is desired to eject a probe 36 from the handle member 34, the eject button 124 is pressed, that is moved toward the right in the direction of an arrow 158 (FIG. 16). This eject motion enables the conical head 120 to contact first and spread to disengage the fingers 134 of the vise tube 132 causing them to lift the spring contacts 142 from the contact areas 60 and 62 (see FIG. 6). The conical head 120 then engages the extremity of the attachment end 42 of the probe 36 forcing it rightwardly against the holding bias of the O-ring seal 154. Thereafter, the probe 36 is completely free of any locking or holding bias, thereby enabling ejection from the handle member, and eventual disposal.

By reason of the construction just described, when the probe 36 assumes the operational position as illustrated in FIG. 15, the physician can rotate the probe housing 92. This motion in turn rotates the probe 36 to align its active region 58 with, and thereby assure proper treatment of, the selected tissue. While there is some amount of, friction between the probe housing 92 and the probe 36 on the one hand and the components of the handle member 34 on the other hand, it is nonetheless minimal. Accordingly, it has been found desirable to provide a drag mechanism 160 (FIGS. 11 and 13) which is engageable with the lock-eject mechanism 90 so as to hold the probe 36 against undesired rotation as during treatment while permitting purposeful rotation as during scanning for locating the proper tissue to be treated.

To this end, the drag mechanism 160 includes a drag pin 162 slidably received in a bore 164 within the pistol grip 84. The bore 164 is generally radially disclosed relative to the vise member 96. The drag pin 162 has a free end engageable with the outer surface of the vise member 96 and is biased into engagement with the vise member by the combination of a compression spring 166 and a drag screw 168. The drag screw 168 is threadedly engaged with the pistol grip 84 at its lowermost end and the spring 166 extends between the drag screw and a spring seat member 170 positioned at the base of the drag pin 162. By reason of the threaded engagement of the drag screw 168 with the pistol grip 84, wear of the free tip end of the drag pin 162 can be accommodated and the spring 166 serves to allow appropriate adjustment. A feature of positive lock can be accomplished between the drag pin 162 and the lock-eject mechanism 90 to prevent rotation of the probe housing 92 by means of a detent or the like. Engagement of the drag pin 162 with the vise member 96 would suffice. Of course, omission of the spring 166 and the extension of the drag pin 162 would alter the sensitivity of adjustment of induced drag on those listed components. As with the constructions which have been previously described, an O-ring 172 is interposed between the drag screw 168 and the bore 164 to prevent entry of dirt and moisture into the interior of the lock-eject mechanism.

It is also noteworthy that other bores 174 and 176 are provided in the pistol grip 84 in order to accommodate the wire leads 148 and a suitable strain relief mechanism 178 is provided at the base of the pistol grip as well (FIG. 11).

Turn now to FIGS. 17-20 for a description of another embodiment of the invention. It is known that some tissue abnormalities create a significantly higher electrical impedance than do others. At the same time, it is desirable to use the same handle member 34 for each of the different treatments which might be performed. FIG. 17 presents typical power versus impedance curves for generators which serve to provide electricity for two different tissue abnormalities. It must be emphasized that the curves are not presented for their numerical accuracy but are provided only to illustrate the concept. Thus, a curve 180 may be typical for a power source or generator 182 (FIG. 18) suitable for the treatment of hemorrhoids (FIG. 1B), its optimum power level occurring at an impedance of 25 ohms. In contrast, a curve 184 may be representative of another source of electricity or generator 186 which provides optimum power at an impedance level of 200 ohms and is suitable for treatment of anal warts (FIG. 1A). It will be appreciated, however, that generators 182 and 186 can be combined into one switchable generator such as indicated at 59 in FIGS. 2 and 11.

Thus, in accordance with the invention, it is intended that a handle member 34A be constructed to receive and hold, alternatively, modified electrosurgical probes 36A and 36B (see especially FIGS. 19A and 19B). Probe 36A may, for example, be a probe designed to treat anal warts and, therefore, requires a generator 186 whose operating characteristics are depicted by the curve 184. Thus, when the attachment end 42A (FIG. 18) is inserted into the bore of the probe housing 92, and the groove 48A slidingly receives the key pin 152 (FIGS. 12, 15, and 16), the contact areas 188 and 190 mechanically and electrically engage associated contacts 142A and 142B suitably mounted on the contact seat member 136 (see FIG. 14). Thus, when the probe 36A is in the operative position on the handle member 34A, its active area is being energized by the generator 186.

In a similar manner, the attachment end of a probe 36B (FIG. 19B), designed for the treatment of hemorrhoids, can be inserted into the bore of the probe housing 92. As the probe 36B is inserted, the longitudinal groove 48B therein is aligned with the key pin 152. When the probe 36B reaches its operative position within the handle 34A, its contact areas 188 and 192 are mechanically and electrically engaged, respectively, with spring contacts 142A and 142C. The active area of the probe 36B is thereby energized by the generator 182 whose operating characteristics are depicted by the curve 180.

It will therefore be understood that in no circumstances can the probe 36A intended for anal warts be accidentally used when treatment of hemorrhoids by means of the probe 36B is intended, and vice versa. The truth table of FIG. 20 clearly presents the fail safe operation insured by the invention.

As seen in FIG. 18, the handle member 34A may be provided with a finger operated trigger 194 which, in a suitable manner, can operate a switch 196 to thereby control the electrical connection to the operating area regardless of which probe is being used. A lamp 198 or other suitable indicator may be employed in conjunction with the switch 196 to provide a positive indication as to whether or not the probe is being energized.

Additionally, it may be desirable for the physician to actively choose the particular treatment and have the handle member 34A so indicate. Thus, a switch 200 mounted on the handle member (FIG. 18) may be moved in the direction of an arrow 202 in the event treatment of hemorrhoids is desired. In this instance, an electrical contact 204 would be moved to the closed position thereby completing the electrical circuit with generator 182 when the probe 36B is held by the handle member 34A in the operating position. Of course, notwithstanding such movement of switch 200, in the event the probe 36A were inserted into the handle member 34A, there would be no completion of the electrical circuit and, in that event, there would be no energization of the active area of the probe.

In a similar fashion, in the event the physician desired to treat anal warts, the switch would be moved in the direction of an arrow 206 to close a contact 208 to thereby complete the circuit to generator 186. In this instance, in the event the probe 36A was accidentally inserted into the handle member 34A, the circuit would not be completed and the active area of the probe would not be energized. Therefore, it will be recognized that the switch 200 will not be effective to energize an improperly inserted probe, but is merely an indication to the physician of the probe whose use was intended. Of course, the switch 200 may be mounted instead, on the generators 182, 186 or on the generator 59. As a further aid to the physician, a lamp 210 or other suitable signal device, possibly audible, may be energized when the contact 204 is closed and, similarly, a lamp 212 may be energized when the contact 208 is closed.

Additionally, due to the inherent darkness of the areas intended for treatment by the invention, a suitable source of illumination 214 may be provided on the handle member 34A such as a light bulb or a fiber optic system. One desirable location for the source 214 would be on the probe housing 92 (FIG. 18) in such a fashion as to allow effective projection of the illumination in the general direction of, and specifically centralized onto, the active region 58 and the tissue being treated thereby. According to a preferred construction, operation of the trigger 194 would cause the source 214 to be energized whenever the electrodes are energized.

Another embodiment of the invention enabling the fail safe use of the disposable probes will now be described with reference to FIGS. 21-24. The information presented in FIG. 17 remains pertinent to this embodiment. FIG. 21 represents a schematic diagram of an electrical circuit similar to the circuit illustrated in FIG. 18 in conjunction with the handle member 34A. For ease of description, the wire leads 148 of FIG. 18 have been further defined in FIG. 21 as 148A, 148B, 148C, respectively, each being connected to its associated contact 142A, 142B, and 142C.

The earlier described embodiment of FIGS. 18-20 related to a system in which the compatability of a probe with the generator output was determined mechanically at the contacts 142. The present embodiment provides a modified system in which compatability is determined electronically at the generator and the output of the generator is automatically corrected, if necessary, according to the type of probe being used.

Thus, as depicted in FIG. 21, power is applied across the leads 148A and 148C by a suitable generator 218 which may be of a known variety capable of operating at two or more distinct impedance levels. For example, the generator 218 may operate at either 25 ohms or at 200 ohms, according to the particular treatment to be performed. Associated with the generator 218 in the circuit 216 is a continuity detector 220 which may be, in essence, an ohmmeter capable of measuring electrical resistance across the leads 148A and 148B. The generator 218 and detector 220 may be provided as a unit indicated by dashed lines 222 in FIG. 21.

In one instance, a probe 36A which may be of the type for treating anal warts and therefore requiring electrical energy at a high impedance level (for example, 200 ohms) may be employed. FIG. 22, which is substantially similar to FIG. 19A, illustrates the probe 36A and the drawing of FIG. 19A is repeated here for ease of explanation. Thus, when the probe 36A is inserted into the probe housing 92, the contact area 188 engages contact 142C and the contact area 190 engages contact 142A. However, in this instance, the contact 142B engages a flattened region 224 on the probe 36A. The flattened region 224 is an unmetallized surface of the dielectric probe such that the detector 220 detects an open circuit across the leads 148A and 148B. When this occurs, the detector 220 informs the generator 218 which, in turn, switches according to the requirement of the detector 220. That is, when the probe 36A is inserted into the probe housing 92, it causes infinite resistance between the leads 148A and 148B. This indicates that the probe is of the type used to treat anal warts and therefore is of the type requiring high impedance (see curve 184 in FIG. 17) and the generator 218 automatically accommodates this requirement.

In the instance in which hemorrhoids are to be treated, using this embodiment, a slightly modified probe 36C (FIGS. 23 and 24) is utilized. The probe 36C is generally of the same construction as the probe 36A with the exception of the addition of an electrode tail 226 extending circumferentially from the contact area 188. Thus, when the probe 36C is inserted into the probe housing 92, the contact 142C engages the contact area 188 and the contact 142A engages the contact area 190, all as previously. In this instance, however, the contact 142B engages the electrode tail 226, thereby completing the circuit across the leads 148A and 148B. This continuity is sensed by the detector 220 which, in turn, informs the generator 218 which switches to the lower impedance level (see curve 180 of FIG. 17) for the appropriate treatment of hemorrhoids. As in the instance of the FIG. 18 embodiment, the switch 196 may be operated to turn power on and off to the active region of the probe. Also, it will be appreciated that the completion of the circuit across the leads 148A and 148B does not in any manner effect the quality of the energy transmitted to the active region of the probe other than to assure that it is at the proper impedance level.

While preferred embodiments of the invention have been disclosed in detail, it should be understood by those skilled in the art that various modifications may b made to the illustrated embodiments without departing from the scope described in the specification and defined in the appended claims

What is claimed is:

1. An electrosurgical probe for use in the treatment of tissue comprising:

an elongated substrate member having a peripheral surface of dielectric material and a longitudinal axis extending between a working end and an attachment end;

at least a pair of electrically isolated electrodes only on said peripheral surface of said substrate member and extending continuously between an active region at said working end and an electrical terminal region at said attachment end for selective connection/disconnection, respectively, to opposite poles of a source of electrical energy; and an outermost dielectric covering on said substrate member at a region extending intermediate said attachment end and said working end and overlying said electrodes as a continuous peripheral band between said active region and said electrical terminal region to electrically isolate said intermediate region.

2. An electrosurgical probe as set forth in claim 1 wherein said electrodes are of a predetermined length at said active region in order to assure a desired degree of focus of treatment in the longitudinal direction.

3. An electrosurgical probe as set forth in claim 1 wherein said substrate member is substantially cylindrical.

4. An electrosurgical probe as set forth in claim 3 wherein said working end is generally cylindrical and has a diameter greater a than that of the remainder of said substrate member.

5. An electrosurgical probe as set forth in claim 1 wherein said peripheral surface is curved in a longitudinal direction at said active region.

6. An electrosurgical probe as set forth in claim 1 wherein said electrodes are of suitable width and spacing for bipolar treatment and are formed on said peripheral surface at said active region so as to cover only that part of said peripheral surface positioned within a defined arc having as its center the longitudinal axis of said substrate member;

whereby the energy being emitted from said electrodes can be directed on a selected area of tissue to be treated.

7. An electrosurgical probe as set forth in claim 1 wherein said electrodes at said active region are omnidirectionally oriented.

8. An electrosurgical probe as set forth in claim 1 wherein each of said electrodes branches into a plurality of electrode fingers at said active region, said fingers of one of said electrodes being interposed with said fingers of the other of said electrodes.

9. An electrosurgical probe as set forth in claim 8 wherein said electrodes are of suitable width and spacing for bipolar treatment and are formed on said peripheral surface at said active region so as to cover only that part of said peripheral surface extending within a predetermined length of said substrate member and positioned within a defined arc having as its center the longitudinal axis of said substrate member;

whereby the energy being emitted from said electrode fingers can be directed on a restricted area of tissue selected for treatment.

10. An electrosurgical probe as set forth in claim 1 wherein said working end of said substrate member terminates at a blunt surface containing said active region lying in a plane generally transverse to the longitudinal axis of said substrate member.

11. Electrosurgical probe apparatus as set forth in claim 10
wherein said electrodes are of suitable width and spacing for bipolar treatment and are formed on said peripheral surface at said active region so as to cover only that part of said peripheral
surface extending within a predetermined width of said blunt surface and positioned within a defined arc having as its center the longitudinal axis of said substrate member;
whereby the energy being emitted from said electrode fingers can be directed on a restricted area of tissue selected for treatment.

12. An electrosurgical probe as set forth in claim 11
wherein said blunt surface lies in a rounded plane generally perpendicular to the longitudinal axis of said substrate member.

13. An electrosurgical probe as set forth in claim 1
wherein said working end is enlarged relative to the remainder of said substrate member; and
wherein said electrodes cover selected portions of said peripheral surface at said active region;
whereby the energy emitted from said electrodes can be directed on a selected tissue area for treatment.

14. An electrosurgical probe as set forth in in claim 1
wherein said working end is enlarged eccentrically relative to the longitudinal axis of said substrate member, said active region lying in a plane generally parallel to and spaced from a plane containing the longitudinal axis of said substrate member.

15. An electrosurgical probe as set forth in claim 14
wherein said peripheral surface at said active region is curved in a longitudinal direction and circumferentially; and
wherein said electrodes cover selected portions of said peripheral surface at said active region;
whereby the energy emitted from said electrodes can be directed on a selected area of tissue to be treated.

16. An electrosurgical probe as set forth in claim 1
wherein said substrate member is adapted to be inserted into a body cavity for movement both along the longitudinal axis and rotationally about the longitudinal axis; and
includes at least one of:
first markings thereon for indicating the depth of said probe within the body cavity and;
second markings thereon for indicating the rotational position of said probe within the body cavity.

17. An electrosurgical probe as set forth in claim 16
wherein in said first markings are located at substantially uniform spaced increments along said substrate member; and
wherein said second markings are located at substantially uniform spaced increments around the periphery of said substrate member.

18. An electrosurgical probe as set forth in claim 16
wherein at least one of said first markings and said second markings are formed of colors which contrast with the remainder of said peripheral surface of said substrate member.

19. An electrosurgical probe as set forth in claim 16
wherein said substrate member has topography on said peripheral surface defining at least one of said first and second markings.

20. An electrosurgical probe as set forth in claim 1
wherein said dielectric covering has a peripheral surface; and
including:
contrast means provided between the peripheral surface of said dielectric covering and said electrodes for improving the visibility of said electrodes.

21. An electrosurgical probe as set forth in claim 1
wherein said electrodes are of a color which contrast with the color of said substrate member.

22. An electrosurgical probe as set forth in claim 1
wherein said substrate member is adapted to be inserted into a body cavity for movement both along the longitudinal axis and rotationally about the longitudinal axis; and
wherein said substrate member has topography on said peripheral surface defining at least one of first markings thereon for indicating the depth of said probe within the body cavity and second markings thereon for indicating the rotational position of said probe within the body cavity; and
wherein said dielectric covering conforms to said topography.

23. Electrosurgical probe apparatus as set forth in claim 1 including:
a handle member for supporting said substrate member in an operative position; and
lock-eject means mounted on said handle member releasably engageable with said substrate member for holding said substrate member in the operative position thereon and for rotating said substrate member about its longitudinal axis.

24. Electrosurgical probe apparatus as set forth in claim 23 including:
switch means on said handle member for energizing said electrodes.

25. An electrosurgical device as set forth in claim 23 including:
indicator means on said handle member for indicating when said electrodes are being energized.

26. An electrosurgical device as set forth in claim 25
wherein said indicator means is at least one of an electric lamp and an audible signal source.

27. Electrosurgical probe apparatus as set forth in claim 23
wherein said lock-eject means includes:
a housing having a bore therethrough mounted on said handle member for rotation about an axis generally coincident with the bore, said housing adapted to receive said attachment end of said substrate member within the bore; and
key means mounted to said housing within the bore and engageable with said substrate member such that rotation of said housing is imparted to said substrate member.

28. Electrosurgical probe apparatus as set forth in claim 27 including:
detent means mounted between said handle and said housing for establishing a reference position of said housing relative to said handle.

29. Electrosurgical probe apparatus as set forth in claim 28 including:
stop means on said handle engageable with said housing for defining extreme
rotational positions of said probe housing relative to the reference position.

30. Electrosurgical probe apparatus as set forth in claim 29 wherein said housing is formed with an arcuate groove therein extending between defined limits; and wherein said stop means is a pin freely received within said groove but engageable with said limits of the groove to thereby define the extreme rotational positions of said housing relative to the reference position.

31. Electrosurgical probe apparatus as set forth in claim 27 wherein said key means includes:
a pin fixed to said housing extending into said bore; and
wherein said substrate member has a longitudinal groove at said attachment end positioned to slidably receive said pin.

32. Electrosurgical probe apparatus as set forth in claim 27
wherein said substrate member has an annular groove at said attachment end; and
wherein said lock-eject means includes:
vise means normally biased into engagement with said groove to maintain said substrate member in the operative position; and
ejection means for overcoming the bias of said vise means and thereby releasing said substrate member from the operative position and moving it to an inoperative position to enable removal of said substrate member from said handle member.

33. Electrosurgical probe apparatus as set forth in claim 32
wherein said ejection means includes:
an eject button mounted on said handle member coaxially aligned with said housing and slidable between an inactive position distant from said housing and an active position proximate to said housing; and
an eject pin fixed to said housing and coaxial therewith engageable with said attachment end of said substrate member such that movement of said eject button from said inactive position to said active position causes movement of said substrate member against the bias of said vise means from the operative position to the inoperative position.

34. Electrosurgical probe apparatus as set forth in claim 33
wherein said ejection means includes:
a spring intermediate said vise means and said eject button biasing said eject button toward the inactive position.

35. Electrosurgical probe apparatus as set forth in claim 32
wherein said vise means is generally cylindrically shaped and has an outer surface and is fixed to said housing for rotation therewith; and
including:
drag means engageable with said outer surface of said vise means for holding said housing and said substrate member supported thereon against undesired rotation while permitting purposeful rotation thereof.

36. Electrosurgical probe apparatus as set forth in claim 35
wherein said drag means includes:
a drag pin slidably received in a bore within said handle member, the bore being radially disposed relative to said vise means, said pin having a free end engageable with said outer surface of said vise means; and
means biasing said free end of said drag pin into engagement with said outer surface of said vise means.

37. Electrosurgical probe apparatus as set forth in claim 36
wherein said biasing means includes:
a drag screw threadedly engaged with said handle member and axially aligned with said drag pin; and
a drag spring intermediate said drag screw and said drag pin;
whereby rotation of said drag screw is effective to adjust the bias of said drag spring against said outer surface of said vise means.

38. Electrosurgical probe apparatus as set forth in claim 27
wherein said substrate member has at least two spaced apart contact surfaces adjacent said attachment end, said electrodes extending, respectively, onto each of said contact surfaces; and
including:
a pair of contact members fixed to said housing and engageable, respectively, with said contact surfaces when said substrate member is in the operative position, said contact members being connected, respectively, to opposite poles of a source of electrical energy.

39. Electrosurgical probe apparatus as set forth in claim 38 including:
key means intermediate said substrate member and said housing for preventing rotational movement therebetween and for aligning said contact surfaces with said contact members.

40. Electrosurgical probe apparatus as set forth in claim 39
wherein said key means includes:
a pin fixed to said housing extending into the bore thereof; and
wherein said substrate member has a longitudinal groove at said attachment and positioned to slidably receive said pin.

41. Electrosurgical probe apparatus as set forth in claim 23
wherein said substrate member has an annular groove at said attachment end; and
wherein said lock-eject means includes:
vise means normally biased into engagement with said groove to maintain said substrate member in the operative position; and
ejection means for overcoming the bias of said vise means and thereby releasing said substrate member from the operative position.

42. Electrosurgical probe apparatus as set forth in claim 23 including:
drag means engageable with said lock-eject means for holding said substrate member against undesired rotation wile permitting purposeful rotation thereof.

43. Electrosurgical probe apparatus as set forth in claim 23 including:
a source of illumination mounted on said handle member and positioned to direct light rays in the direction of said working end when said substrate member is in the operative position.

44. Electrosurgical probe apparatus as set forth in claim 67 including
switch means on said handle member for simultaneously energizing said electrodes and said source of illumination.

* * * * *

UNITED STATES PATENT AND TRADEMARK OFFICE
CERTIFICATE OF CORRECTION

PATENT NO. : 4,823,791

DATED : 4/25/89

INVENTOR(S) : D'Amelio et al.

It is certified that error appears in the above-identified patent and that said Letters Patent is hereby corrected as shown below:

In Col. 20, line 55, Claim 42, delete "wile" and insert therefor --while--

In Col. 20, line 64, Claim 44, delete "67" and insert therefor --43--.

Signed and Sealed this

Fourteenth Day of May, 1991

Attest:

*Attesting Officer*

HARRY F. MANBECK, JR.

*Commissioner of Patents and Trademarks*